United States Patent [19]

Giordano et al.

[11] Patent Number: 4,675,418

[45] Date of Patent: Jun. 23, 1987

[54] PROCESS FOR PREPARING ALKANOIC ACIDS OR ESTERS THEREOF BY REARRANGEMENT OF ALPHA-HALO-KETONES IN PROTIC MEDIUM AND IN THE PRESENCE OF A NON-NOBLE METAL SALT

[75] Inventors: Claudio Giordano, Monza; Giovanni Villa, Monticello Brianza; Fulvio Uggeri, Codogno; Graziano Castaldi, Briona, all of Italy

[73] Assignee: Blaschim S.p.a., Milan, Italy

[21] Appl. No.: 398,586

[22] Filed: Jul. 15, 1982

[30] Foreign Application Priority Data

Jul. 23, 1981 [IT] Italy ................................ 23085 A/81

[51] Int. Cl.$^4$ .................... C07D 333/24; C07C 69/76; C07C 63/36
[52] U.S. Cl. ...................................... 549/79; 560/100; 560/75; 560/56; 562/490; 562/478; 562/466
[58] Field of Search ................. 549/72, 79; 560/100, 560/75, 56; 562/490, 478, 466

[56] References Cited

U.S. PATENT DOCUMENTS 4,414,405 11/1983 Giordano et al. .................... 560/56

FOREIGN PATENT DOCUMENTS 81200210.3 2/1981 European Pat. Off. .
2042543 9/1980 United Kingdom .

OTHER PUBLICATIONS

McOmie Protective Groups in Org. Chem. (1973) pp. 324–332.

*Primary Examiner*—Alan Siegel
*Attorney, Agent, or Firm*—Stevens, Davis, Miller & Mosher

[57] ABSTRACT

Process for preparing alkanoic acid or their esters by rearrangement of alpha-halo-ketones in protic medium and in the presence of a non-noble metal salt.

The protic medium is preferably an aliphatic alcohol having low molecular weight or water and the reaction is carried out at a temperature from 0° C. to the boiling-point of the diluent or of the diluents mixture.

5 Claims, No Drawings

PROCESS FOR PREPARING ALKANOIC ACIDS OR ESTERS THEREOF BY REARRANGEMENT OF ALPHA-HALO-KETONES IN PROTIC MEDIUM AND IN THE PRESENCE OF A NON-NOBLE METAL SALT

The present invention relates to a new process for preparing the aryl-alkanoic acids or esters thereof by rearrangement of alpha-halo-aryl-ketones in protic medium and in the presence of a non-noble metal salt.

More precisely the process according to this invention may be represented by the following scheme

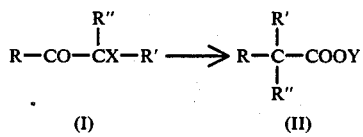

wherein
- R is a radical selected from the group comprising an aryl, substituted aryl, aryl fused with a heterocyclic nucleus, heterocyclic, substituted heterocyclic, heterocyclic fused with an aryl nucleus
- R' and R", which are the same or different, are H, alkyl having 1–10 carbon atoms, benzyl, aryl, substituted aryl, aryl fused with a heterocyclic nucleus, heterocyclic, substituted heterocyclic, heterocyclic fused with an aryl nucleus
- X is a halogen atom
- Y is hydrogen or an alkyl radical having 1–6 carbon atoms.

When the product of formula II is an ester, it can be hydrolyzed by known methods; the corresponding alkanoic acids, which are useful as drugs or intermediates, are thus obtained. Examples of the many alkanoic acids used as drugs for their anti-inflammatory, analgesic and antipyretic properties include ibuprofen, fenclorac, indoprofen, flurbiprofen, suprofen, naproxen, ketoprofen, fenoprofen, piroprofen, eclofenac, xenbucin, diclofenac and tolmetin (Anti-inflammatory Drugs, Springer Verlag 1979, pages 321–323).

Other members of this class, such as the thienylacetic acid can be used as intermediates for preparing semisynthetic penicillins or cefalosporins or for preparing other anti-inflammatory drugs such as thiaprofen acid.

The British patent application No. 2.042.543 published on Sept. 24 1980 discloses a process for preparing the esters of aryl-acetic acids by rearrangement of the corresponding alpha-halo-alkyl-aryl-ketones in the presence of large amounts of silver salts, of an alcohol and a strong acid.

This process is expensive because of the high cost of the silver derivatives which are used.

Furthermore it implies to work in a strongly acid medium with the aim to reduce the formation of alpha-keto-esters and yields are not very high, in fact they never exceed 75%.

In the European patent application No. 81200210.3 of Feb. 24 1981, the applicant discloses a process for preparing the esters of alkanoic acids by rearrangement of the ketals of the corresponding alpha-halo-ketones in the presence of equimolecular or catalytic amounts of a Lewis' acid. This process is more convenient that the former one because it involves the use of little amounts of not very much expensive catalysts besides it allows to obtain very high yields and the reaction doesn't need to be carried out in a strongly acid medium. Nevertheless the use of ketals involves one more step in comparison with the process specified in the British Pat. No. 2.042.543.

Now it has surprisingly been found that the non-noble metal salts catalyze the rearrangement of alpha-halo-ketones of formula I into the esters of alkanoic acids of formula II in protic medium.

The halides of the non-noble transition metal salts, such as the zinc, tin, nickel, cobalt, aluminium etc. chloride, bromide and iodide, are preferably used.

The catalyst can be added just as it is to the reaction mixture or it can be formed "in situ".

The amount of catalyst used for each mole of alpha-halo-ketone ranges from 0.001 to 10 moles.

Protic mediums particularly suitable in the process according to this invention are water and the aliphatic alcohols having low molecular weight.

When water is used, the desired alkanoic acid is directly obtained, whereas when an aliphatic alcohol having low molecular weight is used, the esters of alkanoic acids are obtained.

To the reaction mixture diluents can be added which are protic or aportic, miscible or immiscible with the protic medium which takes part to the reaction.

The reaction temperature is comprised between 0° C. and the boiling-temperature of the reaction mixture, the preferred one is the boiling temperature.

The reaction time varies according to the reactivity of the alpha-halo-ketone, the activity of the catalyst used and the reaction temperature; it can thus range from 10 minutes to 160 hours.

The following examples should not be considered as a limitation upon the scope of the invention but merely as being illustrative and representative thereof.

EXAMPLE 1

2-(4'-methoxy-phenyl)-2-methyl-propionic acid (A) 1-(4'-methoxy-phenyl)-2-bromo-2-methyl-propan-1-one (3.2 g; 0.012 moles) is added under nitrogen and under stirring to a solution of $ZnBr_2$ (25 g; 0.11 moles) in methanol (9 ml) maintained at 85° C. The reaction mixture is maintained at 85° C. and under stirring for 2 hours. The reaction mixture is then cooled to room temperature, poured into water and extracted with methylene chloride (2×50 ml). The collected organic extracts are dried on $Na_2SO_4$, filtered and the solvent is evaporated to afford a residue which according to the I.R. and N.M.R. analysis contains the methyl ester of the 2-(4'-methoxy-phenyl)-2-methyl-propionic acid.

The residue is dissolved in a 30% solution of NaOH (10 ml) in methanol (100 ml).

The mixture is refluxed for 2 hours.

The solvent is evaporated under reduced pressure and the residue is extracted with water (100 ml)-methylene chloride (100 ml) mixture.

The aqueous phase is separated, acidified with conc. HCl and extracted with methylene chloride. The organic extract is dried on sodium sulphate. The evaporation of the solvent under vacuum leaves a residue which by crystallization from petroleum ether/ether affords the 2-(4'-methoxy-phenyl)-2-methyl propionic acid (1.05 g; 0.05 moles) (yield 45%). M.p. 75°–77° C.

(B) Basic carbonated zinc ($2ZnCO_3.3Zn(OH)_2$) (1.89 g; corresponding to 0.017 moles of Zn) is added under stirring and at room temperature, to a mixture of BF₃.2MeOH (4.56 g; 0.034 equivalents acids) and of MeOH (1.4 ml; 0.034 moles). The mixture has been stirred at room temperature for 30'.

1-(4'-methoxy-phenyl)-2-bromo-2-methyl-propan-1-one (2 g; 0.0078 moles) is added to the solution prepared as above.

The reaction mixture is heated at reflux under stirring for 3 hours, and then cooled to room temperature.

It is poured into water (30 ml) and extracted with methylene chloride (2×30 ml). The organic phase is washed with H₂O (2×10 ml) and dried on sodium sulphate. After removal of the solvent under reduced pressure, a hydroalcoholic solution (70 ml MeOH; 30 ml H₂O) is added to the residue containing, on the basis of the spectral determinations, the methylene ester of the 2-methyl-2-(4'-methoxy-phenyl)-propionic acid. The mixture has been heated at 50° C. for 2 hours, poured into H₂O and extracted with CH₂Cl₂. The aqueous phase is acidified with conc. HCl. and extracted with CH₂Cl₂. By evaporation of the solvent under vacuum the 2-methyl-2-(4'-methoxy-phenyl)-propionic acid is obtained (0.75 g; 0.0039 moles; yield 50%).

Operating in a similar way, various alpha-halo-ketones have been allowed to undergo reaction. The results are shown in table I where the alpha-halo-ketones are marked by Roman numbers which have the following meanings:

I: 1-(6'-methoxy-2'-naphthyl)-2-iodo-propan-1-one
II: 1-(6'-methoxy-2'-naphthyl)-2-bromo-propan-1-one
III: 1-(6'-methoxy-2'-naphthyl)-2-chloro-propan-1-one
IV: 1-(2-thienyl)-2-bromo-propan-1-one
V: 1-(4'-isobutyl-phenyl)-2-chloro-propan-1-one
VI: 1-(4'-methoxy-phenyl)-2-bromo-ethan-1-one
VII: 1-(4'-methoxy-phenyl)-2-bromo-2-methyl-propan-1-one The 1-(6'-methoxy-2'-naphthyl)-2-iodo-propan-1-one is a new substance and, as such, it is a further object of the present invention.

It can be prepared as follows:

Potassium iodide (16.6 g; 0.1 moles) is added to a solution of 1-(6'-methoxy-2'-naphthyl)-2-bromo-propan-1-one (2.83 g; 0.01 moles) in acetone (20 ml).

The reaction mixture is brought to reflux temperature for 3 hours, then it is cooled.

It is filtered and the organic phase is concentrated under vacuum. The residue is treated with water and extracted with ethyl ether. By evaporation of the solvent under vacuum it is obtained a residue which crystallizes from methanol (2.38 g; 0.007 moles; 70%) m.p.=106°-107° C.

N.M.R. [CDCl₃/TMS] (ppm)=1.86 (d, 3H, J=7 Hz); 3.54 (S, 3H); 5.01 (q, 1H, J=7 Hz); 6.30-7.65 (m, 6H) I.R.: stretching C=O 1660 cm⁻¹.

TABLE I

| Catalyst (moles) | Protic medium (moles) | Ketone (moles) | Yields (theoretical) | T (C.°) | Time h |
|---|---|---|---|---|---|
| ZnI₂ (0.20) | CH₃OH (0.36) | I (0.02) | 37 | 115 | 5 |
| ZnBr₂ (0.11) | CH₃OH (0.20) | II (0.012) | 55 | 115 | 2 |
| ZnBr₂ (0.33) | H₂O (1.33) | II (0.02) | 10 | 107 | 54 |

TABLE I-continued

| Catalyst (moles) | Protic medium (moles) | Ketone (moles) | Yields (theoretical) | T (C.°) | Time h |
|---|---|---|---|---|---|
| ZnCl₂ (0.11) | CH₃OH (0.20) | III (0.013) | 70 | 115 | 5 |
| ZnCl₂ (0.11) | C₂H₅OH (0.20) | III (0.013) | 10 | 115 | 30 |
| ZnBr₂ (0.5) | CH₃OH (0.88) | IV (0.05) | 21 | 120 | 7 |
| ZnCl₂ (0.5) | CH₃OH (0.88) | V (0.05) | 55 | 115 | 24 |

TABLE II

| Catalyst (moles) | Protic Medium (moles) | Ketone (moles) | Yields (% theoretical) | T (C.°) | Time h |
|---|---|---|---|---|---|
| ZnBr₂ (0.11) | CH₃OH (0.20) | VI (0.012) | 8 | 115 | 6 |
| ZnBr₂ (0.11) | CH₃OH (0.36) | VII (0.02) | 45 | 85 | 2 |
| ZnBr₂ (0.05) | CH₃OH (0.36) | VII (0.012) | 70 | 85 | 2 |
| ZnBr₂ (0.027) | CH₃OH (0.09) | VII (0.012) | 70 | 85 | 2 |
| ZnBr₂ (0.044) | CH₃OH (0.34) | VII (0.12) | 77 | 85 | 0 |
| ZnBr₂ (0.177) | CH₃OH + Toluene (0.5) (10 ml) | II (0.01) | 87 | 92 | 20 |

We claim:

1. Process for preparing alkanoic acids by rearrangement of alpha-halo-ketones according to the following scheme

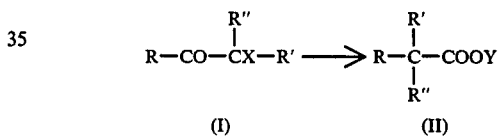

wherein

R is a radical selected from the group consisting of an aryl, substituted aryl, aryl fused with a heterocylic nucleus, heterocyclic, substituted heterocyclic, heterocyclic fused with an aryl nucleus R' and R", which are the same or different, are H, alkyl having 1–10 carbon atoms, benzyl, aryl, substituted aryl, aryl fused with a heterocyclic nucleus, heterocyclic, substituted heterocyclic, heterocyclic fused with an aryl nucleus X is a halogen atom Y is hydrogen or an alkyl radical having 1–6 carbon atoms comprising reacting said alpha-halo-ketone in the presence of a protic medium and of a non-noble metal salt catalyst to obtain a hydrolyzable ester or the corresponding acid.

2. Process according to claim 1, wherein said protic medium is water or an aliphatic alcohol having 1–6 carbon atoms.

3. Process according to claim 1 or claim 2, wherein said metal salt is the salt of a non-noble transistion metal salt.

4. Process according to claim 3, wherein said metal salt is a zinc halide.

5. Process according to claim 1 or claim 2, wherein said reaction is carried out in the presence of a diluent.

* * * * *